United States Patent [19]

Humber et al.

[11] Patent Number: 4,814,344

[45] Date of Patent: Mar. 21, 1989

[54] INDOLE DERIVATIVES

[75] Inventors: David C. Humber, London; Ian H. Coates, Hertford; James A. Bell, Royston; George B. Ewan, Gerrards Cross, all of England

[73] Assignee: Glaxo Group Limited

[21] Appl. No.: 103,645

[22] Filed: Oct. 2, 1987

[30] Foreign Application Priority Data

Oct. 3, 1986 [GB] United Kingdom ............... 86 23819

[51] Int. Cl.⁴ ................. C07D 403/06; C07D 403/14; A61K 31/415
[52] U.S. Cl. .................................. 514/397; 540/598; 514/212; 548/336
[58] Field of Search ................ 548/336; 514/397, 212; 540/598

[56] References Cited

U.S. PATENT DOCUMENTS 4,619,941 10/1986 Wright, Jr. et al. ................ 514/397
4,695,578 9/1987 Coates et al. ........................ 514/397

FOREIGN PATENT DOCUMENTS 0003901  9/1979  European Pat. Off. .
0073663  3/1983  European Pat. Off. .
156603 A 3/1984  European Pat. Off. .
164860 A 5/1984  European Pat. Off. .
175551 A 9/1984  European Pat. Off. .
0171037  2/1986  European Pat. Off. .
2045244 A 10/1980 United Kingdom .
2169292  7/1986  United Kingdom .

OTHER PUBLICATIONS

Tyers et al., Neuroscience Letters, Supplement 29,S68 (1987).
Miner et al., Br. J. Cancer 56 159–162 (1987).
Costall et al., Neuropharmacology 25(11) 1293–1296 (1986).
Donatsch et al., Dr. J. Pharmacol., vol. 81, p. 35(1984).

*Primary Examiner*—John M. Ford
*Attorney, Agent, or Firm*—Bacon & Thomas

[57] ABSTRACT

The invention relates to compounds of formula (I)

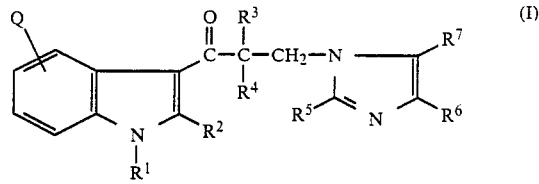

wherein $R^1$ represents a hydrogen atom or a group selected from $C_{1-10}$ alkyl, $C_{3-6}$ alkenyl, $C_{3-10}$ alkynyl, $C_{3-7}$ cycloalkyl, $C_{3-7}$ cycloalkyl $C_{1-4}$ alkyl, phenyl, or phenyl $C_{1-3}$ alkyl, $-CO_2R^{10}$, $-COR^{10}$, $-CONR^{10}R^{11}$ or $-SO_2R^{10}$ (wherein $R^{10}$ and $R^{11}$, which may be the same or different, each represents a hydrogen atom, a $C_{1-6}$ alkyl or $C_{3-7}$ cycloalkyl group, or a phenyl or phenyl$C_{1-4}$ alkyl group, in which the phenyl group is optionally substituted by one or more $C_{1-4}$ alkyl, $C_{1-4}$ alkoxy or hydroxy groups or halogen atoms, with the proviso that $R^{10}$ does not represent a hydrogen atom when $R^1$ represents a group $-CO_2R^{10}$ or $-SO_2R^{10}$);

$R_2$ represents a hydrogen atom or a $C_{1-6}$ alkyl, $C_{3-6}$ alkenyl, $C_{3-7}$ cycloalkyl, phenyl or phenyl $C_{1-3}$ alkyl group;

$R_3$ and $R_4$, which may be the same or different, each represents a hydrogen atom or a $C_{1-6}$ alkyl group;

One of the groups represented by $R^5$, $R^6$ and $R^7$ is a hydrogen atom or a $C_{1-6}$ alkyl, $C_{1-6}$ hydroxyalkyl, $C_{3-7}$ cycloalkyl, $C_{2-6}$ alkenyl, phenyl or phenyl $C_{1-3}$ alkyl group, and each of the other two groups, which may be the same or different, represents a hydrogen atom or a $C_{1-6}$ alkyl group; and Q represents a hydrogen or a halogen atom, or a hydroxy, $C_{1-4}$ alkoxy, phenyl $C_{1-3}$ alkoxy or $C_{1-6}$ alkyl group or a group $-NR^8R^9$ or $-CONR^8R^9$ wherein $R^8$ and $R^9$, which may be the same or different, each represents a hydrogen atom or a $C_{1-4}$ alkyl or $C_{3-4}$ alkenyl group, or together with the nitrogen atom to which they are attached form a saturated 5 to 7 membered ring;

and physiologically acceptable salts and solvates thereof.

The comopounds are potent and selective antagonists of the effect of 5-HT at 5-HT₃ receptors and are useful, for example, in the treatment of psychotic disorders, anxiety, and nausea and vomiting.

14 Claims, No Drawings

INDOLE DERIVATIVES

This invention relates to heterocyclic compounds, to processes for their preparation, to pharmaceutical compositions containing them and to their medical use. In particular the invention relates to compounds which act upon 5-hydroxytryptamine (5-HT) receptors of the type located on terminals of primary afferent nerves.

Compounds having antagonist activity at 'neuronal' 5-HT receptors of the type located on primary afferent nerves have been described previously.

Thus for example published UK patent specification No. 2153821A and published European patent specification No. 191562 disclose tetrahydrocarbazolones of the general formula

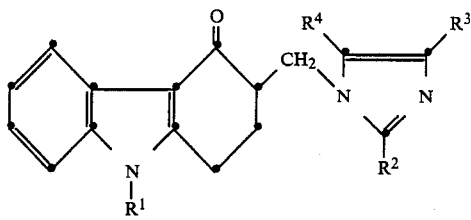

wherein $R^1$ represents a hydrogen atom or a $C_{1-10}$alkyl, $C_{3-7}$cycloalkyl, $C_{3-7}$cycloalkyl $C_{1-4}$alkyl, $C_{3-6}$alkenyl, $C_{3-10}$alkynyl, phenyl or phenyl $C_{1-3}$alkyl group, and one of the groups represented by $R^2$, $R^3$ and $R^4$ is a hydrogen atom or a $C_{1-6}$alkyl, $C_{3-7}$cycloalkyl, $C_{2-6}$alkenyl or phenyl $C_{1-3}$alkyl group and each of the other two groups, which may be the same or different, represents a hydrogen atom or a $C_{1-6}$alkyl group.

We have now found a novel group of compounds which differ in structure from those described previously, and which are potent antagonists of the effect of 5-HT at 5-HT 'neuronal' receptors.

Thus the present invention provides an indole of the general formula (I):

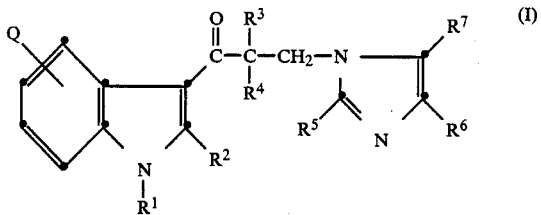

wherein $R^1$ represents a hydrogen atom or a group selected from $C_{1-10}$alkyl, $C_{3-6}$alkenyl, $C_{3-10}$alkynyl, $C_{3-7}$cycloalkyl, $C_{3-7}$cycloalkyl $C_{1-4}$alkyl, phenyl, or phenyl $C_{1-3}$alkyl, $-CO_2R^{10}$, $-COR^{10}$, $-CONR^{10}R^{11}$ or $-SO_2R^{10}$ (wherein $R^{10}$ and $R^{11}$, which may be the same or different, each represents a hydrogen atom, a $C_{1-6}$alkyl or $C_{3-7}$cycloalkyl group, or a phenyl or phenyl $C_{1-4}$alkyl group, in which the phenyl group is optionally substituted by one or more $C_{1-4}$alkyl, $C_{1-4}$alkoxy or hydroxy groups or halogen atoms, with the proviso that $R^{10}$ or $-SO_2R^{10}$);

$R_2$ represents a hydrogen atom or a $C_{1-6}$alkyl, $C_{3-6}$alkenyl, $C_{3-7}$cycloalkyl, phenyl or phenyl $C_{1-3}$alkyl group;

$R^3$ and $R^4$, which may be the same or different, each represents a hydrogen atom or a $C_{1-6}$alkyl group;

one of the groups represented by $R^5$, $R^6$ and $R^7$ is a hydrogen atom or a $C_{1-6}$alkyl, $C_{1-6}$hydroxyalkyl, $C_{3-7}$ cycloalkyl, $C_{2-6}$alkenyl, phenyl or phenyl $C_{1-3}$alkyl group, and each of the other two groups, which may be the same or different, represents a hydrogen atom or a $C_{1-6}$alkyl group; and Q represents a hydrogen or a halogen atom, or a hydroxy, $C_{1-4}$alkoxy, phenyl $C_{1-3}$alkoxy or $C_{1-6}$alkyl group or a group $-NR^8R^9$ or $-CONR^8R^9$ wherein $R^8$ and $R^9$, which may be the same or different, each represents a hydrogen atom or a $C_{1-4}$alkyl or $C_{3-4}$alkenyl group, or together with the nitrogen atom to which they are attached form a saturated 5 to 7 membered ring; and physiological acceptable salts and solvates thereof.

Suitable physiologically acceptable salts of the compounds of general formula (I) include acid addition salts formed with organic or inorganic acids for example, hydrochlorides, hydrobromides, sulphates, phosphates, citrates, succinates, tartrates, fumarates and maleates. The solvates may, for example, be hydrates.

All optical isomers of compounds of general formula (I) and their mixtures including a racemic mixtures thereof, and all the geometric isomers of compounds of formula (I), are embraced by the invention.

Referring to the general formula (I), an alkyl group as such or as part of a group may be a straight chain or branched chain alkyl group, for example, methyl ethyl, propyl, prop-2-yl, butyl, but-2-yl, or 2-methylprop-2-yl, and in the case of $R^1$, $R^2$, $R^3$, $R^4$, $R^5$, $R^6$, $R^7$, $R^{10}$, $R^{11}$ and Q, pentyl, pent-3-yl or hexyl.

A $C_{3-6}$alkenyl group may be, for example, a propenyl or butenyl group. A $C_{3-10}$alkynyl group, may be, for example, a prop-2-ynyl or oct-2-ynyl group. It will be appreciated that when $R^1$ represents a $C_{3-6}$alkenyl or $C_{3-10}$alkynyl group, or $R^8$ or $R^9$ represents a $C_{3-4}$alkenyl group, the double or triple bond may not be adjacent to the nitrogen atom. A phenyl $C_{1-3}$alkyl group, as such or as part of a phenyl $C_{1-3}$alkoxy group, may be, for example, a benzyl, phenethyl or 3-phenylpropyl group. A $C_{3-7}$cycloalkyl group, either alone or as part of a $C_{3-7}$cycloalkyl $C_{1-4}$alkyl group, may be, for example, a cyclopropyl, cyclobutyl, cyclopentyl, cyclohexyl or cycloheptyl group. A $C_{1-4}$alkoxy group may be, for example, a methoxy group. A halogen atom may be, for example, a fluorine, chlorine or bromine atom.

The substituent Q may be at the 4, 5, 6 or 7 position of the indole nucleus.

According to one aspect the invention provides compounds of formula (I) in which $R^1$ represents a hydrogen atom, or a $C_{1-6}$alkyl, $C_{3-6}$alkenyl, $C_{3-10}$alkynyl, $C_{3-7}$cycloalkyl, $C_{3-7}$cycloalkyl $C_{1-4}$alkyl, phenyl or phenyl $C_{1-3}$alkyl group, one of the groups represented by $R^5$, $R^6$ and $R^7$ is a hydrogen atom or a $C_{1-6}$alkyl, $C_{1-6}$hydroxyalkyl, $C_{3-7}$cycloalkyl, $C_{3-6}$alkenyl, phenyl or phenyl $C_{1-3}$alkyl group, and $R^2$, $R^3$, $R^4$ and Q are as defined in formula (I).

A preferred class of compounds represented by the general formula (I) is that wherein $R^1$ represents a hydrogen atom or a $C_{1-3}$ alkyl (e.g. methyl) group. Another preferred class of compounds is that wherein $R^2$ represents a hydrogen atom, a $C_{1-3}$alkyl (e.g. methyl) group or a phenyl group. Another preferred class of compounds is that wherein $R^3$ and $R^4$ are each selected from a hydrogen atom or a methyl group. $R^5$ is preferably a hydrogen atom, a $C_{1-3}$alkyl group (e.g. methyl), a $C_{1-3}$hydroxyalkyl group (e.g. hydroxymethyl) or a phenyl $C_{1-3}$alkyl group (e.g. benzyl). Another preferred class of compounds is that wherein $R^6$ and $R^7$ are each selected from a hydrogen atom or a $C_{1-3}$alkyl (e.g. methyl) group. Another preferred class of compounds is that wherein one of the groups $R^5$, $R^6$ and $R^7$ represents a $C_{1-3}$alkyl (e.g. methyl) group and each of the other two groups represent a hydrogen atom.

Another preferred class of compounds represented by general formula (I) is that wherein Q represents a hydrogen or a halogen (e.g. fluorine) atom. Most preferably Q represents a hydrogen atom. When Q is other than hydrogen it is preferably at the 5-position of the indole ring.

Preferred compounds of the invention are:
3-(2-methyl-1H-imidazol-1-yl)-1-(1-methyl-1H-indol-3-yl)-1-propanone;
3-(4-methyl-1H-imidazol-1-yl)-1-(1-methyl-1H-indol-3-yl)-1-propanone;
2,2-dimethyl-3-(2-methyl-1H-imidazol-1-yl)-1-(1-methyl-1H-indol-3-yl)-1-propanone;
and physiologically acceptable salts and solvates thereof.

It will be appreciated that the invention extends to other physiologically acceptable equivalents of the compounds according to the invention, i.e. physiologically acceptable compounds which are converted in vivo into the parent compound of formula (I).

Compounds of the invention are potent and selective antagonists of 5-HT-induced depolarisation of the rat isolated vagus nerve preparation and thus act as potent and selective antagonists of the 'neuronal' 5-HT receptor type located on primary afferent nerves. Receptors of this type are now designated as 5-HT$_3$ receptors. Such receptors are also believed to be present in the central nervous system. 5-HT occurs widely in the neuronal pathways in the central nervous system and disturbance of these 5-HT containing pathways is known to alter aspects of behaviour such as mood, psychomotor activity, appetite and memory.

Compounds of formula (I), which antagonise the effect of 5-HT at 5-HT$_3$ receptors, are useful in the treatment of conditions such as psychotic disorders (e.g. schizophrenia and mania); anxiety; and nausea and vomiting. Compounds of formula (I) are also useful in the treatment of gastric stasis; symptoms of gastrointestinal dysfunction such as occur with dyspepsia, peptic ulcer, reflux oesophagitis, flatulence and irritable bowel syndrome; migraine; and pain.

Unlike existing drug treatments for these conditions, the compounds of the invention, because of their high selectivity for 5-HT$_3$ receptors, would not be expected to produce undesirable side effects. Thus, for example, neuroleptic drugs may exhibit extrapyramidal effects, such as tardive dyskinesia, and benzodiazepines may cause dependence.

According to another aspect, the invention provides a method of treatment of a human or animal subject suffering from a psychotic disorder such as schizophrenia or mania; or from anxiety; nausea or vomiting; gastric stasis; symptoms of gastrointestinal dysfunction such as dyspepsia, reflux oesophagitis, peptic ulcer, flatulence and irritable bowel syndrome; migraine; or pain, which comprises administering an effective amount of a compound of formula (I) or a physiologically acceptable salt or solvate thereof.

Accordingly, the invention also provides a pharmaceutical composition which comprises at least one compound selected from compounds of the general formula (I), and their physiologically acceptable salts and solvates e.g. hydrates, for use in human or veterinary medicine, and formulated for administration by any convenient route.

Such compositions may be formulated in conventional manner using one or more physiologically acceptable carriers and/or excipients.

Thus the compounds according to the invention may be formulated for oral, buccal, parenteral or rectal administration or in a form suitable for administration by inhalation or insufflation (either through the mouth or nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxylpropyl methylcellulose); fillers (e.g. lactose, microcrystallline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of the invention may be formulated for parenteral administration by injection. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may also be formulated in rectal compositions such as suppositories or retention enemas, e.g. containing conventional suppository bases such as cocoa butter or other glycerides.

In addition to the formulations described previously, the compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For administration by inhalation the compounds according to the invention are conveniently delivered in the form of an aerosol spray presentation from pressurised packs or a nebuliser, with the use of a suitable propellant, e.g. dichlorodifluoromethane, trichlorofluoromethane, dichlorotetrafluoroethane, carbon dioxide or other suitable gas. In the case of a pressurised aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

A proposed dose of the compounds of the invention for administration to man (of approximately 70 kg body weight) is 0.05 to 100 mg, preferably 0.1 to 50 mg (e.g. 0.5 to 20 mg) of the active ingredient per unit dose which could be administered, for example, 1 to 4 times per day. It will be appreciated that it may be necessary to make routine variations to the dosage, depending on the age and condition of the patient. The dosage will also depend on the route of administration.

Compounds of general formula (I) and physiologically acceptable salts or solvates thereof may be prepared by the general methods outlined hereinafter. In the following description, the groups $R^1$ to $R^7$ and Q are as defined for compounds of general formula (I) unless otherwise stated.

According to a first general process (A), a compound of general formula (I) may be prepared by reacting a compound of formula (II):

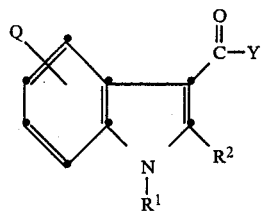

(II)

(wherein Y represents a reactive substituent) or a protected derivative thereof, with an imidazole of formula (III)

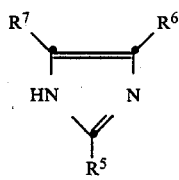

(III)

or a salt thereof, followed where necessary by deprotection.

Examples of compounds of formula (II) employed as starting materials in the process (A) include compounds wherein Y represents a group selected from an alkenyl group $-CR^3=CH_2$ or a group of formula $-CR^3R^4CH_2Z$ where Z represents a readily displaceable atom or group such as a halogen atom (e.g. chlorine, bromine or iodine) an acyloxy group (e.g. trifluoroacetyloxy or acetoxy) or a sulphonyloxy group (e.g. trifluoromethanesulphonyloxy, p-toluenesulphonyloxy or methanesulphonyloxy); a group $-N^+R^{12}R^{13}R^{14}X^-$, where $R^{12}$, $R^{13}$ and $R^{14}$, which may be the same or different, represent lower alkyl (e.g. methyl), aryl (e.g. phenyl) or aralkyl (e.g. benzyl), or $R^{12}$ and $R^{13}$ together with the nitrogen atom to which they are attached may form a 5- to 6-membered ring (e.g. a pyrrolidine ring) and $X^-$ represents an anion such as a halide ion (e.g. chloride, bromide or iodide); or a group $-NR^{12}R^{13}$ where $R^{12}$ and $R^{13}$ are as defined above, for example $-N(CH_3)_2$.

When Y represents the group $CR^3=CH_2$, the process may conveniently be carried out in a suitable solvent, examples of which include esters (e.g. ethyl acetate), ketones (e.g. acetone), amides (e.g. dimethylformamide) and alcohols (e.g. ethanol), or mixtures thereof. The process may be effected at a temperature of, for example, 20° to 100° C.

When Y represents the group $-CR^3R^4CH_2Z$, where Z is a halogen atom or an acyloxy or sulphonyloxy group, the process may conveniently be carried out in a suitable solvent such as an amide (e.g. dimethylformamide), an alcohol (e.g. methanol or industrial methylated spirit), or a haloalkane (e.g. dichloromethane), at a temperature of from $-10°$ to $+50°$ C.

The reaction including a compound of formula (II) where Y represents the group $-CR^3R^4CH_2Z$ where Z is the group $-N^+R^{12}R^{13}R^{14}X^-$ may conveniently be carried out in a suitable solvent, such as an amide (e.g. dimethylformamide), a ketone (e.g. acetone) or an ether (e.g. dioxan), at a temperature of from 20° to 150° C.

The reaction including a compound of formula (II) where Y represents the group $-CR^3R^4CH_2Z$, where Z is the group $-NR^{12}R^{13}$, may conveniently be carried out in a suitable solvent such as water or an alcohol (e.g. methanol), or mixtures thereof, or an amide (e.g. dimethylformamide), at a temperature of from 20° to 150° C.

The starting materials of formula (II) wherein Y represents the group $CR^3=CH_2$ may be prepared from compounds of formula (II) where Y represents the group $-CR^3R^4CH_2N^+R^{12}R^{13}R^{14}X^-$ (wherein at least one of $R^3$ and $R^4$ represents a hydrogen atom) by reaction with a base in a suitable solvent. Examples of bases include alkali metal hydroxides (e.g. potassium hydroxide) or alkali metal carbonates or hydrogen carbonates (e.g. sodium hydrogen carbonate).

Quaternary salts of formula (II) may themselves be formed from the corresponding tertiary amine of formula (II) where Y represents the group $-CR^3R^4CH_2NR^{12}R^{13}$ by reaction with an alkylating agent such as methyl iodide or dimethyl sulphate, if preferred in a suitable solvent (e.g. methanol) or an amide (e.g. dimethylformamide). The tertiary amine may be prepared by reaction of an indole of formula (IV):

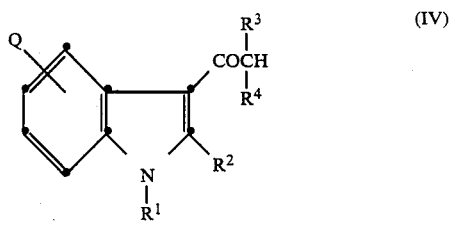

(IV)

with formaldehyde and the corresponding secondary amine, if desired in a suitable solvent such as an alcohol (e.g. ethanol).

The starting materials of formula (II) where Y represents —CH$_2$Z where Z is a halogen atom or an acyloxy or a sulphonyloxy group may be prepared from the corresponding hydroxymethyl derivative of formula (V):

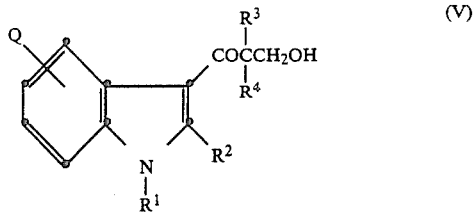

Thus, the compounds where Z is a halogen atom may be obtained by reacting a compound of formula (V) with a halogenating agent such as thionyl chloride or a phosphorus trihalide (e.g. phosphorus trichloride). The compounds where Z is an acyloxy or a sulphonyloxy group may be prepared by reacting a compound of formula (V) with an appropriate acylating or sulphonylating agent such as an anhydride or a sulphonyl halide (e.g. sulphonyl chloride).

The compounds where Z is a halogen atom may also be prepared by reacting a halomagnesylindole (e.g. a bromomagnesylindole), with the appropriate acyl halide (e.g. 3-chloropropionyl chloride), using conventional techniques.

Compounds of formula (V) may be prepared by reacting an indole of formula (IV) with formaldehyde, preferably in a suitable solvent such as an alcohol (e.g. ethanol), and preferably in the presence of a base.

According to another general process (B), a compound of formula (I) may be converted into another compound of formula (I) using conventional techniques. Such conventional techniques include alkylation, acylation, hydrogenation or acid-catalysed cleavage.

Alkylation according to general process (B) may be effected for example on a compound of formula (I) where one or more of R$^1$, R$^3$, R$^4$, R$^8$ and R$^9$ represent a hydrogen atom, or Q represents a hydroxy group.

The term 'alkylation' also includes the introduction of other groups such as cycloalkyl or alkenyl groups. Thus, for example, a compound of formula (I) in which R$^1$ represents a C$_{1-10}$alkyl, C$_{3-7}$cycloalkyl, C$_{3-6}$alkenyl, C$_{3-10}$alkynyl, C$_{3-7}$cycloalkyl C$_{1-4}$alkyl or phenyl C$_{1-3}$alkyl group may be prepared from the corresponding compound in which R$^1$ represents a hydrogen atom, or a compound in which R$^3$ and/or R$^4$ represents a C$_{1-6}$alkyl group may be prepared from a compound in which R$^3$ and/or R$^4$ represents a hydrogen atom. Similarly a compound of formula (I) in which Q represents a C$_{1-4}$alkoxy group may be prepared by alkylating the corresponding compound in which Q represents a hydroxyl group.

The above alkylation reactions may be effected using the appropriate alkylating agent selected from compounds of formula R$^{15}$W where R$^{15}$ represents a C$_{1-10}$alkyl, C$_{3-7}$cycloalkyl, C$_{3-6}$alkenyl, C$_{3-10}$alkynyl, C$_{3-7}$cycloalkyl C$_{1-4}$alkyl or phenyl C$_{1-3}$alkyl group, and W represents a leaving atom or group such as a halogen atom or an acyloxy or sulphonyloxy group as previously defined for Z; or a sulphate of formula (R$^{15}$)$_2$SO$_4$.

The alkylation reaction is conveniently carried out in an inert organic solvent such as a substituted amide (e.g. dimethylformamide), an ether (e.g. tetrahydrofuran), an aromatic hydrocarbon (e.g. toluene) or dimethylsulphoxide, preferably in the presence of a base. Suitable bases include, for example, alkali metal hydrides (e.g. sodium or potassium hydride), alkali metal amides (e.g. sodium amide or lithium diisopropylamide), alkali metal carbonates (e.g. sodium or potassium carbonate) or an alkali metal alkoxide (e.g. sodium or potassium methoxide, ethoxide or t-butoxide). The reaction may conveniently be effected at a temperature in the range −80° to +100° C., preferably −80° to 50° C.

Acylation according to general process (B) may be used to prepare compounds of formula (I) wherein R$^1$ represents —CO$_2$R$^{10}$, —COR$^{10}$, —CONR$^{10}$R$^{11}$ or —SO$_2$R$^{10}$, from a compound of formula (I) wherein R$^1$ represents a hydrogen atom. The acylation reactions may be effected according to conventional procedures using an appropriate acylating agent.

Hydrogenation according to general process (B) may be used to convert an alkenyl or an alkynyl substituent into an alkyl substituent, or an alkynyl into an alkenyl substituent.

Hydrogenation may be effected using conventional procedures, for example using hydrogen in the presence of a noble metal catalyst (e.g. palladium, Raney nickel, platinum or rhodium). The catalyst may be supported on, for example, charcoal, or alternatively a homogeneous catalyst such as tris(triphenylphosphine)rhodium chloride may be used. The hydrogenation will generally be effected in a solvent such as an alcohol (e.g. ethanol), an ether (e.g. dioxan), or an ester (e.g. ethyl acetate), and at a temperature in the range −20° to +100° C., preferably 0° to 50° C.

Acid-catalysed cleavage according to general process (B) may be used, for example, to prepare a compound of formula (I) in which Q represents a hydroxyl group from the corresponding compound in which Q represents a C$_{1-4}$ alkoxy group. The reaction may be effected using a Lewis acid such as boron tribromide or aluminium trichloride, in a solvent such as a halogenated hydrocarbon (e.g. dichloromethane). The reaction temperature may conveniently be in the range −80° to +100° C.

It should be appreciated that in the above transformations it may be necessary or desirable to protect any sensitive groups in the molecule of the compound in question to avoid undesirable side reactions. For example, it may be necessary to protect the keto group, for example, as a ketal or a thioketal. It may also be necessary to protect the indole nitrogen atom, for example with an arylmethyl (e.g. benzyl or trityl) group.

Thus according to another general process (C), a compound of formula (I) may be prepared by the removal of any protecting groups from a protected form of a compound of formula (I). Deprotection may be effected using conventional techniques such as those described in 'Protective Groups in Organic Synthesis' by Theodora W. Greene (John Wiley and Sons, 1981).

For example a ketal such as an alkyleneketal group may be removed by treatment with a mineral acid such as hydrochloric acid. A thioketal group may be cleaved by treatment with a mercuric salt, (e.g. mercuric chloride), in a suitable solvent, such as ethanol. An arylmethyl N-protecting group may be cleaved by treatment with sodium in liquid ammonia or by hydrogenolysis in the presence of a catalyst (e.g. palladium on charcoal) and a trityl group may also be cleaved by acid hydrolysis (e.g. using dilute hydrochloric or acetic acid).

Where it is desired to isolate a compound of the invention as a salt, for example a physiologically acceptable salt, this may be achieved by reacting the compound of formula (I) in the form of the free base with an appropriate acid, preferably with an equivalent amount, in a suitable solvent such as alcohol (e.g. ethanol or methanol), an ester (e.g. ethyl acetate) or an ether (e.g. tetrahydrofuran).

Physiologically acceptable salts may also be prepared from other salts, including other physiologically acceptable salts, of the compound of formula (I) using conventional methods.

Physiologically acceptable equivalents of a compound of formula (I) may be prepared according to conventional methods.

Individual enantiomers of the compounds of the invention may be obtained by resolution of a mixture of enantiomers (e.g. a racemic mixture) using conventional means, such as an optically active resolving acid; see for example 'Stereochemistry of Carbon Compounds' by E. L. Eliel (McGraw Hill 1962) and 'Tables of Resolving Agents' by S. H. Wilen.

The methods indicated above for preparing the compounds of the invention can be used as the last main step in the preparative sequence. The same general methods can be used for introduction of the desired groups at an intermediate stage in the stepwise formation of the required compound, and it will be appreciated that these general methods can be combined in different ways in such multi-stage processes. The sequence of the reactions in multi-stage processes should of course be chosen so that the reaction conditions used do not affect groups in the molecule which are desired in the final product.

The invention is illustrated by the following Examples. All temperatures are in °C.

Column chromatography was carried out either in the conventional manner using silica (Merck, Kieselgel 60, Art. 7734 or 7747) or by flash chromatography on silica (Merck 9385), and thin layer chromatography (t.l.c.) was carried out on silica (Macherly-Nagel, Polygram). The following abbreviations define the solvent systems used for chromatography:

| (A) Dichloromethane-ethanol-0.88 ammonia | 100:8:1 |
| (B) Dichloromethane-ethanol-0.88 ammonia | 200:8:1 |

Organic extracts were dried over sodium sulphate or magnesium sulphate. Light petroleum refers to that fraction having b.p. 60°–80° C. The following abbreviations are used: DMF-dimethylformamide, THF-tetrahydrofuran, IMS-industrial methylated spirits.

Intermediate 1

1-(1-Methyl-1H-indol-3-yl)-3-(pyrrolidin-1-yl)-1-propanone hydrochloride

A mixture of 1-(1-methyl-1H-indol-3-yl)-1-ethanone (4 g), paraformaldehyde (1.045 g) and pyrrolidine hydrochloride (2.26 g) in ethanol (70 ml) was stirred and heated at reflux for 24 h. The mixture was then evaporated to dryness and water (400 ml) was added and the mixture was filtered. The filtrate was brought to pH 10 with 0.88 ammonia solution and extracted with ethyl acetate (2×400 ml). The combined organic extracts were washed with water (50 ml), dried and evaporated to leave an oil (5.52 g), which was dissolved in ether (100 ml) and hydrogen chloride gas was bubbled through the solution. The crystalline precipitate was filtered off and dissolved in water (250 ml) and the solution was brought to pH 10 with 0.88 ammonia solution and extracted with ethyl acetate. The extract was washed with water, dried and evaporated to leave an oil (3.80 g) which was purified by column chromatography eluting with methanol to give an oil (3.09 g). This was dissolved in ethyl acetate and the solution was extracted with 0.5M hydrochloric acid solution (2×50 ml). The extract was evaporated to leave a solid which on trituration with acetone yielded the title compound (3.145 g), m.p. 186°–187°.

Intermediate 2

1-(1-Methyl-1H-indol-3-yl)-3-(pyrrolidin-1-yl)-1-propanone methiodide

A solution of 1-(1-methyl-1H-indol-3-yl)-3-(pyrrolidin-1-yl)-1-propanone hydrochloride (2.25 g) in water (100 ml) was basified with 0.88 ammonia solution (2 ml) and the resulting suspension was extracted with ethyl acetate (100 ml+50 ml). The combined organic extracts were washed with water (30 ml), dried and evaporated to leave an oil (1.88 g), which was dissolved in methanol (10 ml) and the solution was cooled in an ice-bath. Iodomethane (0.91 ml) was added and the mixture was stirred at 0°–5° for 30 min. and then at room temperature for 50 min. when a precipitate formed. The solid was collected by filtration, washed with ether and dried to give the title compound, (1.40 g), m.p. 181°–182° (decomp.). The mother liquors were evaporated to leave an oil which was dissolved in methanol (8 ml) and iodomethane (0.7 ml).

After 80 min. the precipitate formed was filtered off, washed with ether and dried to give a further batch of the title compound (0.21 g).

Intermediate 3

1-(1-Methyl-1H-indol-3-yl)-1-prop-2-enone

A solution of 1-(1-methyl-1H-indol-3-yl)-3-(pyrrolidin-1-yl)-1-propanone methiodide (1.60 g) in methanol (400 ml) was treated with 0.1M methanolic potassium hydroxide solution (40 ml). The solution was stirred for 1.25 h and then diluted with water (2 l) and extracted with dichloromethane (2×250 ml). The combined organic extracts were washed with 0.5M hydrochloric acid (100 ml), dried and evaporated to leave a solid (0.78 g) which was purified by column chromatography eluting with dichloromethane to give the title compound (0.51 g). A sample (117 mg) was crystallised from ethyl acetate to give the title compound (77 mg), m.p. 106°–107°.

Intermediate 4

3-(Dimethylamino)-1-(2-phenyl-1H-indol-3-yl)-1-propanone methiodide

3-Dimethylamino-(2-phenyl-1H-indole-3-yl)-1-propanone (2 g) was stirred with iodomethane (30 ml) and the mixture was heated at reflux for 21 h. The white precipitate formed was filtered off, washed with ether and dried to give title compound (3.37 g) m.p. 136°–138°.

Intermediate 5

1-(2-phenyl-1H-indol-3-yl)-1-prop-2-enone 3-(Dimethylamino)-1-(2-phenyl-1H-indol-3-yl)-1-propanone methiodide (3.11 g) was stirred in methanol (200 ml) and the mixture was treated with 0.1M methanolic potassium hydroxide (72 ml). The mixture was stirred for a further 25 min, diluted with water (1.4 l) and extracted with dichloromethane (3×500 ml). The combined, dried organic extracts were evaporated to give a foam which was dissolved in ethyl acetate (250 ml) and the solution was filtered. The filtrate was evaporated to leave a solid (1.6 g) which was purified by column chromatography eluting with chloroform to give a solid (1.06 g) which was crystallised from ethyl acetate:light petroleum (1:1) to give the title compound (0.92 g), m.p. 145°–146°.

Intermediate 6

3-(Dimethylamino)-1-(1-methyl-1H-indol-3-yl)-1-propanone

A mixture of 1-(1-methyl-1H-indol-3-yl)-1-ethanone (46.16 g), paraformaldehyde (12.0 g) and dimethylamine hydrochloride (21.65 g) in ethanol (970 ml) was stirred and heated at reflux for 24 h. The mixture was diluted with water (3.5 l) and filtered. The filtrate was basified with 0.88 ammonia solution and extracted with ethyl acetate (3×665 ml). The combined organic extracts were washed with water, dried and evaporated to give title compound (57.24 g) as an oil, $\lambda_{max}$ (EtOH) 245.5 nm ($\epsilon$15,820), $\lambda_{max}$ 303.5 nm ($\epsilon$15,680), $\lambda_{inf}$ 249.5 nm ($\epsilon$15,015).

Intermediate 7

3-Chloro-1-(2-methyl-1H-indol-3-yl)-1-propanone

A solution of ethyl bromide (0.37 ml) in ether (5 ml) was added to magnesium (0.12 g) and the mixture was stirred at reflux for 3.5 h. The mixture was cooled and a solution of 2-methyl-1H-indole (0.65 g) in ether (20 ml) was added dropwise. The mixture was then heated at reflux for 2 h, cooled and a solution of 3-chloropropionyl chloride (0.47 ml) in ether (5 ml) was added. The reaction was immediately quenched by the addition of ammonium chloride (0.52 g) in water (5 ml) and the aqueous phase was extracted with ether (3×25 ml). The combined organic extracts were washed with water (2×25 ml), dried and evaporated to leave a solid (0.85 g). Ether (10 ml) was added and the solid was filtered off and dried to give the title compound (0.19 g), m.p. 137°–140°.

Intermediate 8

3-(Dimethylamino)-1-(2-methyl-1H-indol-3-yl)-1-propanone

A solution of dimethylamine in IMS (33% w/v; 8 ml) was added to 3-chloro-1-(2-methyl-1H-indol-3-yl)-1-propanone (404 mg) and the mixture was left for 30 min. when a solid was precipitated. The mixture was refrigerated for 15 min. and the solid was filtered off and dried to give the title compound (207 mg). The mother liquors were evaporated to leave a solid which was partly dissolved in ethyl acetate (20 ml). Water (20 ml) was added and the solid remaining out of solution dissolved. The organic phase was extracted with 2M hydrochloric acid (3×20 ml) and the combined acidic extracts were brought to pH 10 with 0.88 ammonia solution. The mixture was extracted with ethyl acetate (3×25 ml), and the combined, dried organic extracts were evaporated to leave a solid which was crystallised from ethanol. The crystals were combined to give the title compound (386 mg), m.p. 172°–175°.

Intermediate 9

1-(1-Methyl-2-phenyl-1H-indol-3-yl)-1-ethanone

Dimethylsulphoxide (12 ml) and potassium carbonate (3.31 g) were stirred for 10 min. and then 1-(2-phenyl-1H-indol-3-yl)-1-ethanone (1.41 g) was added and stirring was continued for a further 40 min. Iodomethane (0.75 ml) was added and the mixture was stirred for 2.75 h. Water (30 ml) was added and the mixture was extracted with ether (3×40 ml). The combined organic extracts were washed with water (4×40 ml), dried, and evaporated to leave an oil which was crystallised from cyclohexane to give the title compound (1.27 g), m.p. 76°–77°.

Intermediate 10

3-(Dimethylamino)-1-(1-methyl-2-phenyl-1H-indol-3-yl)-1-propanone

A mixture of 1-(1-methyl-2-phenyl-1H-indol-3-yl)-1-ethanone (1.0 g), paraformaldehyde (191 mg) and dimethylamine hydrochloride (347 mg) in ethanol (15 ml) was stirred and heated at reflux for 30 h. The mixture was then evaporated and the residue was treated with water (150 ml) and then filtered. The filtrate was brought to pH 10 with 0.88 ammonia solution and the suspension obtained was extracted with ethyl acetate (2×125 ml). The combined organic extracts were washed with water (50 ml), dried and evaporated to leave an oil (997 mg) which was purified by column chromatography eluting with methanol to give an oil (0.50 g). This was dissolved in ether (50 ml) and extracted with 0.5M hydrochloric acid (2×50 ml). The combined acidic extracts were brought to pH 10 with 0.88 ammonia solution and the resulting precipitate was extracted with ethyl acetate (2×70 ml). The combined organic extracts were washed with water (40 ml), dried and evaporated to leave an oil (0.444 g) which was purified by preparative t.l.c. eluting with methanol to give the title compound (0.30 g) as an oil, which crystallised from light petroleum, m.p. 55°–57°.

Intermediate 11

3-(Dimethylamino)-1-(1,2-dimethyl-1H-indol-3-yl)-1-propanone

A mixture of 1-(1,2-dimethyl-1H-indol-3-yl)-1-ethanone (0.9 g), paraformaldehyde (0.43 g) and dimethylamine hydrochloride (1.2 g) in ethanol (60 ml) was heated at reflux for 18 h, cooled, and the solvent evaporated in vacuo. The residue was partitioned between sodium carbonate (2N; 50 ml) and ethyl acetate (2×50 ml) and the combined organic extracts were dried and evaporated in vacuo to give an oil. This oil was chromatographed eluting with System A to give the title compound, which on standing gave crystals (0.9 g), m.p. 96°–98°.

Intermediate 12

1-(5-Methoxy-1-methyl-1H-indol-3-yl)-1-ethanone

Phosphoryl chloride (1.05 ml) was added dropwise to ice-cooled dimethylacetamide (10 ml) and the solution was stirred, in ice, for 5 min. A solution of 5-methoxy-1- methyl-1H-indole (1.4 g) in dimethylacetamide (5 ml) was added dropwise, and the resulting solution was stirred at 85° for 2 h, then cooled, and partitioned between sodium carbonate (2N; 100 ml) and ethyl acetate (2×100 ml). The combined organic extracts were washed with water (2×100 ml), dried and evaporated in vacuo. The residue was purified by FCC eluting with ethyl acetate to give a solid which was crystallised from a mixture of ethyl acetate and hexane to give the title compound (0.6 g), m.p. 167°-168°.

Intermediate 13

3-(Dimethylamino)-1-(5-methoxy-1-methyl-1H-indol-3-yl)-1-propanone hydrochloride hemihydrate A mixture of 1-(5-methoxy-1-methyl-1H-indol-3-yl)-1-ethanone (0.23 g), paraformaldehyde (0.07 g) and dimethylamine hydrochloride (0.2 g) in ethanol (20 ml) was heated at reflux for 24 h, cooled, and the solvent was evaporated in vacuo. The residue was partitioned between sodium carbonate (2N; 50 ml) and ethyl acetate (2×50 ml). The combined organic extracts were dried and evaporated in vacuo to give an oil, which was purified by FCC eluting with System A to give the free base of the title compound as an oil. This was dissolved in absolute ethanol (5 ml) acidified with ethanolic hydrogen chloride, and the salt was precipitated by the addition of excess dry ether (100 ml). The salt was filtered off and dried in vacuo to give the title compound (0.1 g), m.p. 210°-211°.

Intermediate 14

1-(1,5-Dimethyl-1H-indol-3-yl)-1-ethanone

Phosphoryl chloride (2.1 ml) was added dropwise to ice-cooled, dimethylacetamide (20 ml) and the solution was stirred at ca.0° for 10 min. A solution of 1,5-dimethyl-1H-indole (2.5 g) in dimethylacetamide (5 ml) was added, and the resulting solution was stirred at 85° for 2 h, then cooled, and partitioned between sodium carbonate (2N; 500 ml) and ethyl acetate (2×300 ml). The combined organic extracts were washed with water (300 ml), dried and evaporated in vacuo to give an oil, which was purified by FCC eluting with chloroform:hexane (1:1) to give the title comound as a solid (1.5 g), m.p. 119°-121°.

Intermediate 15

3-(Dimethylamino)-1-(1,5-dimethyl-1H-indol-3-yl)-1-propanone hydrochloride

A mixture of 1-(1,5-dimethyl-1H-indol-3-yl)-1-ethanone (1.4 g), paraformaldehyde (0.7 g) and dimethylamine hydrochloride (1.8 g) in ethanol (60 ml) was heated at reflux for 24 h, cooled, and the solvent was evaporated in vacuo. The residue was partitioned between sodium carbonate (2N; 75 ml) and ethyl acetate (2×75 ml). The combined organic extracts were dried and evaporated in vacuo to give an oil, which was purified by FCC eluting with System A to give the free base of the title compound as an oil (0.8 g). A sample of the free base (0.1 g) was dissolved in hot ethanol (10 ml) acidified with ethanolic hydrogen chloride, and diluted with hot ethyl acetate (40 ml). On cooling, the salt crystallised out and was filtered off, and dried in vacuo to give the title compound (0.1 g), m.p. 225°-228°.

Intermediate 16

1-(5-Fluoro-1-methyl-1H-indol-3-yl)-1-ethanone

Phosphoryl chloride (1.1 ml) was added dropwise to ice-cooled dimethylacetamide (10 ml) and the resulting solution was stirred at ca.0° for 10 min. A solution of 5-fluoro-1-methyl-1H-indole (1.3 g) in dimethylacetamide (5 ml) was added, and the resulting solution was stirred at 100° for 2 h, then cooled, and partitioned between sodium carbonate (2N; 100 ml) and ethyl acetate (2×50 ml). The combined organic extracts were washed with water (50 ml), dried and evaporated in vacuo to give a solid which was purified by FCC eluting with hexane:ethyl acetate (1:1) to give the title compound (0.48 g), m.p. 158°-160°.

Intermediate 17

3-(Dimethylamino)-1-(5-fluoro-1-methyl-1H-indol-3-yl)-1-propanone hydrochloride

A solution of 1-(5-fluoro-1-methyl-1H-indol-3-yl)-1-ethanone (0.9 g) in ethanol (60 ml) containing paraformaldehyde (0.45 g) and dimethylamine hydrochloride (1.2 g) was heated at reflux for 18 h, cooled, and the solvent was evaporated in vacuo. The residue was partitioned between sodium carbonate (2N; 100 ml) and ethyl acetate (2×100 ml). The combined organic extracts were dried and evaporated in vacuo to give an oil, which was purified by FCC eluting with System A to give the free base of the title compound as an oil (0.55 g). A sample (0.1 g) was dissolved in absolute ethanol (5 ml) acidified with ethanolic hydrogen chloride, and the salt was precipitated by the addition of dry ether (ca. 150 ml). The salt was filtered off, and dried in vacuo to give the title compound (0.1 g), m.p. 184°-185°.

Intermediate 18

3-(Dimethylamino)-1-(1-methyl-1H-indol-3-yl)-1-propanone methiodide

A stirred solution 3-dimethylamino-1-(1-methyl-1H-indol-3yl)-1-propanone (57.24 g) in methanol (280 ml) was treated with iodomethane (31 ml). After 4 h the deposited solid was collected, washed with methanol and dried to give the title compound (68.68 g), m.p. 205°-207°.

EXAMPLE 1

3-(1H-Imidazol-1-yl)-1-(1-methyl-1H-indol-3-yl)-1-propanone

Imidazole (0.433 g) was added to a solution of 1-(1-methyl-1H-indol-3-yl)-1-prop-2-enone (0.393 g) in ethyl acetate (12 ml) and the mixture was stirred and heated at reflux for 2.25 h. The mixture was cooled and allowed to stand for 18 h at room temperature. The resulting precipitate was filtered off, washed with ethyl acetate (2 ml) and ether (10 ml) and dried to give the title compound (0.317 g), m.p. 121°-123°; $\lambda_{max}$ (EtOH) 245.5 nm ($\epsilon$14,080), $\lambda_{inf}$ 248 nm ($\epsilon$13,750), $\lambda_{inf}$ 258 nm ($\epsilon$9,400), $\lambda_{max}$ 304 nm ($\epsilon$14,000).

EXAMPLE 2

3-(1H-Imidazol-1-yl)-1-(1H-indol-3-yl)-1-propanone

By a similar procedure to that described in Example 1, 1-(1H-indol-3-yl)-1-prop-2-enone (0.4 g) was reacted with imidazole (0.8 g) to give the title compound (0.314 g), m.p. 194°-197°; $\lambda_{max}$ (EtOH) 242.5 nm ($\epsilon$12,900) $\lambda_{inf}$ 259 nm ($\epsilon$9,090) $\lambda_{max}$ 299.5 nm ($\epsilon$12,390).

EXAMPLE 3

3-(1H-Imidazol-1-yl)-1-(2-phenyl-1H-indol-3-yl)-1-propanone

Imidazole (0.58 g) was dissolved in a solution of 1-(2-phenyl-1H-indol-3-yl)-1-prop-2-enone (0.4 g) in ethyl acetate (14 ml) and the mixture was stirred at room temperature for 3.25 h and then heated at reflux for 2.75 h. The mixture was cooled, allowed to stand for 18 h and was then evaporated to dryness. The solid residue was stirred with methanol (25 ml) for 10 min. filtered off, washed with ether and dried to leave a solid (0.312 g). This was crystallised from methanol to give the title compound (198 mg), 200°–201° (decomp.); $\lambda_{inf}$(EtOH) 249.5 nm ($\epsilon$19,360) $\lambda_{max}$ 254 nm ($\epsilon$20,217), $\lambda_{max}$ 307 nm ($\epsilon$13,180).

EXAMPLE 4

3-(1H-Imidazol-1-yl)-1-(1-methyl-1H-indol-3-yl)-1-propanone

A stirred solution of 3-(dimethylamino)-1-(1-methyl-1H-indol-3-yl)-1-propanone (57.24 g) in methanol (280 ml) was treated with iodomethane (31 ml). After 4 h the deposited solid was collected, washed with methanol and dried to give 3-(dimethylamino)-1-(1-methyl-1H-indol-3-yl)-1-propanone methiodide (68.68 g).

A mixture of the methiodide (45.0 g) and imidazole (43.0 g) in dimethylformamide (1000 ml) was heated at 100°–110° for 7 l h. The resulting solution was allowed to cool overnight then diluted with water (6 l) and extracted with ethyl acetate. The combined organic extracts were washed with water, dried and concentrated whereupon a solid separated (15.3 g). This recrystallised from ethyl acetate to give the title compound in two crops (14.29 g), m.p. 124°–126°; $\lambda_{max}$ (EtOH) 245.5 nm ($\epsilon$14,440), $\lambda_{inf}$ 250 nm ($\epsilon$13,855), $\lambda_{max}$ 305 nm ($\epsilon$14,340) and (0.90 g), m.p. 121°–124°, identical with the material obtained in Example 1.

Examples 5 to 8 were prepared in a similar manner to that described in Example 4.

EXAMPLE 5

3-(1H-Imidazol-1-yl)-1-(1H-indol-3-yl)-1-propanone 3-(Dimethylamino)-1-(1H-indol-3-yl)-1-propanone was converted to the methiodide (12.75 g) which was then reacted with imidazole (12.75 g) to give the title compound (4.67 g), m.p. 193°–197°; $\lambda_{max}$ (EtOH) 242.5 nm ($\epsilon$11,130), $\lambda_{inf}$ 257.5 nm ($\epsilon$9,120), $\lambda_{max}$ 299 nm ($\epsilon$12,420), identical with the material obtained in Example 2.

EXAMPLE 6

3-(1H-Imidazol-1-yl)-1-(2-phenyl-1H-indol-3-yl)-1-propanone 3-(Dimethylamino)-1-(2-phenyl-1H-indol-3-yl)-1-propanone was converted to the methiodide (36 g) which was then reacted with imidazole (34 g) to give a solid which was crystallised from methanol, to give the title compound (15.40 g), m.p. 206°–208°; $\lambda_{max}$ (EtOH) 255 nm ($\epsilon$19,650), $\lambda_{max}$ 307.5 nm ($\epsilon$12,840), identical with the material obtained in Example 3.

EXAMPLE 7

3-(1H-Imidazol-1-yl)-1-(2-methyl-1H-indol-3-yl)-1-propanone 3-(Dimethylamino)-1-(2-methyl-1H-indol-3-yl)-1-propanone was converted to the methiodide (1.50 g) which was then reacted with imidazole (2.67 g) to give a solid which was crystallised from methanol to give the title compound (0.65 g), m.p. 196°–197°; $\lambda_{max}$ (EtOH) 244 ($\epsilon$12,920), $\lambda_{max}$ 268.5 nm ($\epsilon$10,460), $\lambda_{max}$ 302.5 ($\epsilon$11,400).

EXAMPLE 8

3-(1H-Imidazol-1-yl)-1-(1-methyl-2-phenyl-1H-indol-3-yl)-1-propanone 3-(Dimethylamino)-1-(1-methyl-2-phenyl-1H-indol-3-yl)-1-propanone was converted to the methiodide (5.50 g) which was then reacted with imidazole (5.50 g) to give a solid which was crystallised from ethyl acetate to give the title compound (2.91 g), m.p. 159°–162°; $\lambda_{max}$ (EtOH) 251 nm ($\epsilon$19,470), $\lambda_{max}$ 307 nm ($\epsilon$13,800).

EXAMPLE 9

3-(2-Methyl-1H-imidazol-1-yl)-1-(1,2-dimethyl-1H-indol-3-yl)-1-propanone hydrochloride Iodomethane (0.2 ml) was added to a stirred solution of 3-(dimethylamino)-1-(1,2-dimethyl-1H-indol-3-yl)-1-propanone (0.75 g) in dry DMF (15 ml) and the solution was stirred at room temperature for 10 min. 2-Methyl-1H-imidazole (1.2 g) was added and the suspension was stirred at 100° for 3 h. The solution was cooled and partitioned between sodium carbonate (2N; 100 ml) and ethyl acetate (2×100 ml). The combined organic extracts were washed with water (100 ml), dried and evaporated in vacuo and the residue was purified by FCC eluting with System A to give the free base of the title compound as a solid. This was dissolved in hot absolute ethanol acidified with ethanolic hydrogen chloride which on cooling gave the title compound (0.46 g), m.p. 234°–235°.

Analysis Found: C, 63.9; H, 6.4; N, 13.05. $C_{17}H_{19}N_3O$. HCl requires C, 64.25; H, 6.3; N, 13.2%.

EXAMPLE 10

1-(5-Methoxy-1-methyl-1H-indol-3-yl)-3-(2-methyl-1H-imidazol-1-yl)-1-propanone hydrochloride By a procedure similar to that described in Example 9, 3-(dimethylamino)-1-(5-methoxy-1-methyl-1H-indol-3-yl)-1-propanone (1.2 g) was converted to the methiodide which was then reacted with 2-methyl-1H-imidazole (1.9 g) to give the free base of the title compound as a solid. This was dissolved in hot ethanol (20 ml) acidified with ethanolic hydrogen chloride, and diluted with hot ethyl acetate (150 ml). On cooling, the salt crystallised out, and was filtered off, and dried in vacuo to give the title compound (1.0 g), m.p. 211°–213°.

Analysis Found: C, 60.8; H, 6.1; N, 12.5. $C_{17}H_{19}N_3O_2$.HCl requires C, 61.2; H, 6.0; N, 12.6%.

Examples 11 and 12 were prepared in a similar manner to that described in Example 10 from the appropriate intermediate.

EXAMPLE 11

3-(2-Methyl-1H-imidazol-1-yl)-1-(1,5-dimethyl-1H-indol-3-yl)-1-propanone hydrochloride 3-(Dimethylamino)-1-(1,5-dimethyl-1H-indol-3-yl)-1-propanone (0.7 g) was converted to the methiodide which was then reacted with 2-methyl-1H-imidazole (1.2 g) to give the free base of the title compound. Salt formation gave the title compound (0.53 g), m.p. 218°–220°.

Analysis Found: C, 64.4; H, 6.5; N, 13.1. $C_{17}H_{19}N_3O.HCl$ requires C, 64.25; N, 6.3; N, 13.2%.

EXAMPLE 12

1-(5-Fluoro-1-methyl-1H-indol-3-yl)-3-(2-methyl-1H-imidazol-1-yl)-1-propanone hydrochloride 3-(Dimethylamino)-1-(5-fluoro-1-methyl-1H-indol-3-yl)-1-propanone (0.45 g) was converted to the methiodide which was then reacted with 2-methyl-1H-imidazole (0.75 g) to give the free base of the title compound. Salt formation gave the title compound (0.35 g), m.p. 238°–239° C.

Analysis Found: C, 59.6; H, 5.3; N, 12.9. $C_{16}H_{16}FN_3O.HCl$ requires C, 59.7; H, 5.3; N, 13.1%.

EXAMPLE 13

3-(2-Methyl-1H-imidazol-1-yl)-1-(1-methyl-1H-indol-3-yl)-1-propanone hydrochloride A suspension of Intermediate 18 (5.0 g) in dry DMF (25 ml) containing 2-methyl-1H-imidazole (5.0 g) was heated at 100° for 3 h, cooled, and partitioned between sodium carbonate (2N; 250 ml) and ethyl acetate (2×150 ml). The combined organic extracts were washed with water (2×100 ml), dried and evaporated in vacuo to give a solid which was purified by column chromatography eluting with System A to give the free base of the title compound as a solid. This was dissolved in hot absolute ethanol (25 ml) and acidified with ethanolic hydrogen chloride. On cooling, the title compound was deposited as a crystalline solid (1.92 g), m.p. 216°–218°.

Analysis Found: C, 63.3; H, 6.0; N, 13.75. $C_{16}H_{17}N_3O.HCl$ requires C, 63.3; H, 6.0; N, 13.8%.

Examples 14 to 17 were prepared in a similar manner to Example 13, from Intermediate 18 and the appropriate imidazole.

EXAMPLE 14

3-(2-Ethyl-1H-imidazol-1-yl)-1-(1-methyl-1H-indol-3-yl)-1-propanone hydrochloride (2.6 g); m.p. 202°–204°, from Intermediate 18 (5 g) and 2-ethyl-1H-imidazole (5 g).

Analysis Found: C, 63.7; H, 6.4; N, 13.1. $C_{17}H_{19}N_3O.HCl$ requires C, 64.2; H, 6.35; N, 13.2%.

EXAMPLE 15

1-(1-Methyl-1H-indol-3-yl)-1-[2-(1,1-dimethylethyl)-1H-imidazol-1-yl]1-propanone hydrochloride (0.1 g); m.p. 160°–163°, from Intermediate 18 (0.7 g) and 2-(1,1-dimethylethyl)-1H-imidazole (0.7 g).

Analysis Found: C, 61.9; H, 6.5; N, 11.0. $C_{19}H_{23}N_3O.HCl.1.25H_2O$ requires C, 61.9; H, 6.2; N, 11.4%.

EXAMPLE 16

1-(1-Methyl-1H-indol-3-yl)-3-[2-(1-methylethyl)-1H-imidazol-1-yl]1-propanone hydrochloride (0.55 g), m.p. 181°–183°, from Intermediate 18 (1.5 g) and 2-(1-methylethyl)-1H-imidazole (1.5 g).

Analysis Found: C, 64.1; H, 6.9; N, 12.35. $C_{18}H_{21}N_3O.HCl.0.25H_2O$ requires C, 64.3; H, 6.7; N, 12.5%.

EXAMPLE 17

1-(1-Methyl-1H-indol-3-yl)-3-[2-(phenylmethyl)-1H-imidazol-1-yl]-1-propanone hydrochloride (0.7 g), m.p. 178°–179°, from Intermediate 18 (2.0 g) and 2-(phenylmethyl)-1H-imidazole (2.0 g).

Analysis Found: C, 65.8; H, 6.0; N, 10.0. $C_{22}H_{21}N_3O.HCl.1.2H_2O$ requires C, 65.8; H, 6.1; N, 10.5%.

EXAMPLE 18

3-(4,5-Dimethyl-1H-imidazol-1-yl)-1-(1-methyl-1H-indol-3-yl)-1-propanone hydrochloride A stirred suspension of Intermediate 18 (4.65 g) and 4,5-dimethylimidazole hydrochloride (1.2 g) in dry DMF (20 ml) was heated at 100° for 2 h. Potassium carbonate (0.89 g) was added and the stirred mixture was heated for a further 18 h. The solvent was evaporated under reduced pressure and the residue was partitioned between ethyl acetate (150 ml) and sodium carbonate (2N; 50 ml). The organic phase was washed with water (100 ml), dried and evaporated under reduced pressure to give a gum, which was purified by column chromatography eluting with System B. This was converted to the hydrochloride salt with ethanolic hydrogen chloride to give the title compound as prisms (0.61 g) which was crystallised form propan-2-ol, m.p. 220°–222°.

Analysis Found: C, 63.2; H, 6.9; N, 12.9. $C_{17}H_{19}N_3O.HCl.0.3H_2O$ requires C, 63.1; H, 6.4; N, 13.0%.

EXAMPLE 19

3-(4-Methyl-1H-imidazol-1-yl)-1-(1-methyl-1H-indol-3-yl)-1-propanone hydrochloride A solution of Intermediate 18 (1.0 g) and 4-methylimidazole (1.16 g) in dry DMF (40 ml) was stirred at 95° for 4.5 h. The solution was evaporated to dryness under reduced pressure and the residue was dissolved in ethyl acetate (75 ml), washed with water (4×50 ml), dried and evaporated under reduced pressure to afford a gum (0.8 g) which was purified by column chromatography eluting with System A to give a solid (0.61 g). This was shown by n.m.r. to be a mixture of the 4-methyl and 5-methyl isomers. The required 4-methyl isomer was isolated by h.p.l.c. (Gilson Autoprep, Zorbax-Sil support on a 25 cm×21.2 mm column eluting with hexane:ethanol:0.880 ammonia (800:300:1)) as an oil (0.159 g). This was dissolved in ethyl acetate (20 ml) and treated with excess ethereal hydrogen chloride. The solid was filtered off and washed with anhydrous ether (30 ml) and dried to give the title compound (0.148 g), m.p. 193°–195°.

Analysis Found: C, 62.0; H, 5.7; N, 13.4. $C_{16}H_{17}N_3O.HCl.0.3H_2O$ requires C, 62.0; H, 6.0; N, 13.6%.

EXAMPLE 20

1-(1-Methyl-1H-indol-3-yl)-3-(2-phenyl-1H-imidazol-1-yl)-1-propanone hydrochloride By a procedure similar to that described in Example 13, Intermediate 18 (5 g) was reacted with 2-phenylimidazole (5 g) and the resulting free base of the title compound was purified by FCC eluting with ethyl acetate. Salt formation according to Example 10 gave the title compound (1.82 g), m.p. 195°–197°.

Analysis Found: C, 68.65; H, 5.7; N, 11.2. $C_{21}H_{19}N_3O \cdot HCl$ requires C, 68.9; H, 5.5; N, 11.5%.

EXAMPLE 21

1-(1-Methyl-1H-indol-3-yl)-3-[4-(1,1-dimethylethyl)-1H-imidazol-1-yl]1-propanone hydrochloride A suspension of Intermediate 18 (2.01 g) in anhydrous DMF (15 ml) was treated with 4-(1,1-dimethylethyl)-imidazole (0.67 g) and was stirred at 95°–100° for 4.25 h. Removal of the solvent under reduced pressure gave a residue which was mixed with water (50 ml) and extracted with ethyl acetate (6×40 ml). Evaporation of the combined, dried organic extracts yielded a gum (1.08 g). Column chromatography eluting with System B gave a semi-solid (0.66 g) which was triturated with anhydrous ether (25 ml)/light petroleum (5 ml) to give the free base of the title compound as a solid (0.392 g). A sample of the free base (0.3 g) was dissolved in anhydrous ether (10 ml) and treated with excess ethereal hydrogen chloride. Ethanol (5 ml) was added and the resultant solution was evaporated to dryness under reduced pressure to give a foam. Trituration of the foam with anhydrous ether gave the title compound (0.293 g), m.p. 175°–180°.

Water Analysis Found: 0.99%. Theory: 0.97% (for $0.19H_2O$) Analysis Found: C, 65.3; H, 7.2; N, 11.9. $C_{19}H_{23}N_3O \cdot HCl \cdot 0.188H_2O$ requires C, 65.3; H, 7.0; N, 12.0%.

EXAMPLE 22

3-[2-(Hydroxymethyl)-1H-imidazol-1-yl]-1-(1-methyl-1H-indol-3-yl)-1-propanone hydrochloride By a procedure similar to that described in Example 13, Intermediate 18 (0.5 g) was reacted with 1H-imidazole-2-methanol hydrochloride (0.5 g) in dry DMF (10 ml) containing triethylamine (5 ml). The resulting free base of the title compound was purified by FCC eluting with dichloromethane:ethanol: 0.88 ammonia (50:8:1). Salt formation according to Example 10 gave the title compound (0.14 g), m.p. 181°–182°.

Analysis Found: C, 60.3; H, 5.65; N, 12.9. $C_{16}H_{17}N_3O_2 \cdot HCl$ requires C, 60.1; H, 5.7; N, 13.0%.

EXAMPLE 23

3-(1H-Imidazol-1-yl)-1-(1,2-dimethyl-1H-indol-3-yl)-1-propanone

A mixture of 3-(1H-imidazol-yl)-1-(2-methyl-1H-indol-3-yl)-1-propanone (148 mg), and potassium carbonate (0.7 g) in dimethylsulphoxide (5 ml) was stirred for 1 h and treated with iodomethane (0.10 g). The mixture was stirred for a further 4 h then diluted with water and extracted with ether (200 ml total). The combined organic extracts were washed with water, dried and evaporated to give the title compound which was crystallised from ethyl acetate to give a solid (80 mg), m.p. 151°–152°; $\lambda_{max}$ (EtOH) 246.5 nm ($\epsilon$12,940), $\lambda_{max}$ 268.5 nm ($\epsilon$8,740), $\lambda_{max}$ 306.5 nm ($\epsilon$12,215).

EXAMPLE 24

2-Methyl-3-(2-methyl-1H-imidazol-1-yl)-1-(1-methyl-1H-indol-3-yl)-1-propanone n-Butyllithium (1.6M in hexane; 10 ml) was added dropwise to a stirred solution of diisopropylamine (1.6 ml) in dry THF (40 ml) at 0° under nitrogen. After 40 min at 0° the reaction was cooled to −70° and treated dropwise with a solution of 3-(2-methyl-1H-imidazol-1-yl)-1-(1-methyl-1H-indol-3-yl)-1-propanone (2.7 g) in dry THF (150 ml) over 45 min. After a further 30 min a solution of iodomethane (0.7 ml) in hexamethylphosphoramide (1.5 ml) was added, and the suspension was allowed to warm to room temperature over 2.5 h. The suspension was partitioned between sodium carbonate (2N; 150 ml) and ethyl acetate (2×100 ml). The combined organic extracts were dried and evaporated in vacuo to give an oil which was purified by column chromatography eluting with System B to give the free base of the title compound as an oil (2.05 g). A sample (0.5 g) of the free base was dissolved in absolute ethanol (5 ml) acidified with ethanolic hydrogen chloride, and the salt was precipitated by diluting with excess dry ether (ca. 200 ml). The salt was filtered off, and dried in vacuo to give the title compound (0.25 g), m.p. 205°–207°.

Analysis Found: C, 63.9; H, 6.3; N, 12.9. $C_{17}H_{19}N_3O \cdot HCl$ requires C, 64.25; H, 6.3; N, 13.2%.

EXAMPLE 25

2,2-Dimethyl-3-(2-methyl-1H-imidazol-1-yl)-1-(1-methyl-1H-indol-3-yl)-1-propanone hydrochloride A solution of 2-methyl-3-(2-methyl-1H-imidazol-1-yl)-1-(1-methyl-1H-indol-3-yl)-1-propanone (0.5 g) in dry THF (10 ml) was added dropwise, under nitrogen, to a cooled (−70°) suspension of potassium hydride in THF (10 ml) and the resulting suspension was stirred at ca. −70) for 10 min. A solution of iodomethane (0.12 ml) in hexamethylphosphoramide (1.0 ml) was added, and the suspension was allowed to warm to room temperature over 20 min. The suspension was partitioned between sodium carbonate (2N; 50 ml) and ethyl acetate (2×50 ml) and the combined organic extracts were dried and evaporated in vacuo to give an oil which was purified by column chromatography eluting with dichloromethane:ethanol: 0.88 ammonia (400:30:3) to give the free base of the title compound. This was dissolved in ethanolic hydrogen chloride (2 ml) adn the solvent was removed in vacuo. Trituration with dry ether gave the title compound (0.06 g), m.p. 206°–208° (decomp.).

Analysis Found: C, 60.3; H, 7.0; N, 11.8. $C_{18}H_{21}N_3O \cdot HCl1.5H_2O$ requires C, 60.2; H, 7.0; N, 11.7%.

The following examples illustrate pharmaceutical formulations according to the invention. The term "active ingredient" is used herein to represent a compound of formula (I).

TABLETS FOR ORAL ADMINISTRATION

Tablets may be prepared by the normal methods such as direct compression or wet granulation.

The tablets may be film coated with suitable film forming materials, such as hydroxypropyl methylcellulose, using standard techniques. Alternatively the tablets may be sugar coated.

| Direct Compression | |
|---|---|
| Tablet | mg/tablet |
| Active Ingredient | 10.00 |
| Calcium Hydrogen Phosphate BP* | 77.75 |
| Croscarmellose Sodium NF | 1.8 |
| Magnesium Stearate BP | 0.45 |
| Compression weight | 90.0 |

*of a grade suitable for direct compression.

The active ingredient is passed through a 60 mesh sieve, blended with the calcium hydrogen phosphate, croscarmellose sodium and magnesium stearate. The resultant mix is compressed into tablets using a Manesty F3 tablet machine fitted with 5.5 mm, flat bevelled edge punches.

Tablets of other strengths may be prepared by altering the ratio of active ingredient to excipients or the compression weight and using punches to suit.

| INJECTION FOR INTRAVENOUS ADMINISTRATION | |
|---|---|
| | mg/ml |
| Active Ingredient | 1.0 |
| Sodium Chloride BP | as required |
| Water For Injection BP to | 1.0 ml |

Sodium chloride may be added to adjust the tonicity of the solution and the pH may be adjusted, using acid or alkali, to that of optimum stability and/or facilitate solution of the active ingredient. Alternatively suitable buffer salts may be used.

The solution is prepared, clarified and filled into appropriate size ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen or other suitable gas.

We claim:

1. A Compound of formula (I):

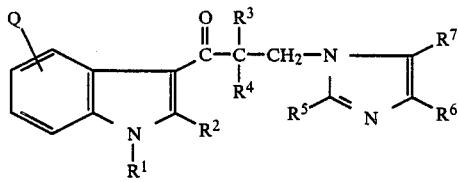

(I)

wherein $R^1$ represents a hydrogen atom or a group selected from $C_{1-10}$ alkyl, $C_{3-6}$ alkenyl, $C_{3-10}$ alkynyl, $C_{3-7}$ cycloalkyl, $C_{3-7}$ cycloalkyl $C_{1-4}$ alkyl, phenyl, or phenyl $C_{1-3}$ alkyl, $-CO_2R^{10}$, $-COR^{10}$, $-CONR^{10}R^{11}$ or $-SO_2R^{10}$ (wherein $R^{10}$ and $R^{11}$, which may be the same or different, each represents a hydrogen atom, a $C_{1-6}$ alkyl or $C_{3-7}$ cycloalkyl group, or a phenyl or phenyl $C_{1-4}$ alkyl group, in which the phenyl group is optionally substituted by one or more $C_{1-4}$ alkyl, $C_{1-4}$ alkoxy or hydroxy groups or halogen atoms, with the proviso that $R^{10}$ does not represent a hydrogen atom when $R^1$ represents a group $-CO_2R^{10}$ or $-SO_2R^{10}$);

$R_2$ represents a hydrogen atom or a $C_{1-6}$ alkyl, $C_{3-6}$ alkenyl, $C_{3-7}$ cycloalkyl, phenyl or phenyl $C_{1-3}$ alkyl group;

$R_3$ and $R_4$, which may be the same or different, each represents a hydrogen atom or a $C_{1-6}$ alkyl group;

One of the groups represented by $R^5$, $R^6$ and $R^7$ is a hydrogen atom or a $C_{1-6}$ alkyl, $C_{1-6}$ hydroxyalkyl, $C_{3-7}$ cycloalkyl, $C_{2-6}$ alkenyl, phenyl or phenyl $C_{1-3}$ alkyl group, and each of the other two groups, which may be the same or different, represents a hydrogen atom or a $C_{1-6}$ alkyl group; and Q represents a hydrogen or a halogen atom, or a hydroxy, $C_{1-4}$ alkoxy, phenyl $C_{1-3}$ alkoxy or $C_{1-6}$ alkyl group or a group $-NR^8R^9$ or $-CONR^8R^9$ wherein $R^8$ and $R^9$, which may be the same or different, each represents a hydrogen atom or a $C_{1-4}$ alkyl or $C_{3-4}$ alkenyl group, or together with the nitrogen atom to which they are attached form a saturated 5 to 7 membered ring;

and physiologically acceptable salts and solvates thereof.

2. A compound according to claim 1 in which $R^1$ represents a hydrogen atom or a $C_{1-3}$ alkyl group.

3. A compound according to claim 1 in which $R^2$ represents a hydrogen atom, a $C_{1-3}$ alkyl group or a phenyl group.

4. A compound according to claim 1 in which $R^3$ and $R^4$ are each selected from a hydrogen atom and a methyl group.

5. A compound according to claim 1 in which $R^5$ represents a hydrogen atom, a $C_{1-3}$ alkyl group, a $C_{1-3}$ hydroxyalkyl group or a phenyl $C_{1-3}$ alkyl group.

6. A compound according to claim 1 in which $R^6$ and $R^7$ are each selected from a hydrogen atom and a $C_{1-3}$ alkyl group.

7. A compound according to claims 1 in which one of the groups $R^5$, $R^6$ and $R^7$ represents a $C_{1-3}$ alkyl group and each of the other two groups represents a hydrogen atom.

8. A compound according to claim 1 in which Q represents a hydrogen or a halogen atom.

9. A compound selected from:
3-(2-methyl-1H-imidazol-1-yl)-1-(1-methyl-1H-indol-3-yl)-1-propanone;
3-(4-methyl-1H-imidazol-1-yl)-1-(1-methyl-1H-indol-3-yl)-1-propanone;
2,2-dimethyl-3-(2-methyl-1H-imidazol-1-yl)-1-(1-methyl-1H-indol-3-yl)-1-propanone;
and physiologically acceptable salts and solvates thereof.

10. A compound according to claim 1 in which $R^1$ represents a hydrogen atom, or a $C_{1-6}$ alkyl, $C_{3-6}$ alkenyl, $C_{3-10}$ alkynyl, $C_{3-7}$ cycloalkyl, $C_{3-7}$ cycloalkyl $C_{1-4}$ alkyl, phenyl or phenyl $C_{1-3}$ alkyl group, one of the groups represented by $R^5$, $R^6$ and $R^7$ is a hydrogen atom or a $C_{1-6}$ alkyl, $C_{1-6}$—hydroxyalkyl, $C_{3-7}$ cycloalkyl, $C_{3-6}$ alkenyl, phenyl or phenyl $C_{1-3}$ alkyl group, and $R^2$, $R^3$, $R^4$ and Q are as defined in claim 1.

11. A pharmaceutical composition for the treatment of a condition selected from psychotic disorders, anxiety, and nausea and vomiting comprising at least one compound of formula (I) as defined in claim 1 or a physiologically acceptable salt or solvate thereof in an amount effective to relieve said condition together with at least one physiologically acceptable carrier or excipient.

12. A method of treating a condition selected from psychotic disorders, anxiety and nausea and vomiting which comprises administering to a patient an effective amount to relieve said condition of a compound of formula (I) as defined in claim 1 or a physiologically acceptable salt or solvate thereof.

13. A pharmaceutical composition for the treatment of a condition selected from gastric stasis, symptoms of gastrointestinal dysfunction, migraine and pain comprising at least one compound of formula (I) as defined in claim 1 or a physiologically acceptable salt or solvate thereof in an amount effective to relieve said condition together with at least one physiologically acceptable carrier or excipient.

14. A method of treating a condition selected from gastric stasis, symptoms of gastrointestinal dysfunction, migraine and pain which comprises administering to a patient an effective amount to relieve said condition of a compound of formula (I) as defined in claim 1 or a physiologically acceptable salt or solvate thereof.

* * * * *